(12) United States Patent
Barthelat et al.

(10) Patent No.: US 10,376,611 B2
(45) Date of Patent: Aug. 13, 2019

(54) MULTILAYERED BONE GRAFT AND METHOD OF MAKING SAME

(71) Applicant: THE ROYAL INSTITUTION FOR THE ADVANCEMENT OF LEARNING/MCGILL UNIVERSITY, Montreal (CA)

(72) Inventors: Francois Barthelat, Montreal (CA); Michael Tanzer, Hampstead (CA); Sacha Cavelier, Montreal (CA)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 524 days.

(21) Appl. No.: 15/044,414

(22) Filed: Feb. 16, 2016

(65) Prior Publication Data

US 2016/0235536 A1    Aug. 18, 2016

Related U.S. Application Data

(60) Provisional application No. 62/116,612, filed on Feb. 16, 2015.

(51) Int. Cl.
*A61F 2/28* (2006.01)
*A61L 27/12* (2006.01)
(Continued)

(52) U.S. Cl.
CPC ............. *A61L 27/12* (2013.01); *A61F 2/28* (2013.01); *A61F 2/2875* (2013.01);
(Continued)

(58) Field of Classification Search
None
See application file for complete search history.

(56) References Cited

U.S. PATENT DOCUMENTS 5,017,627 A * 5/1991 Bonfield ............. A61F 2/30965
523/115
5,084,051 A * 1/1992 Tormala ................ A61L 31/129
428/688
(Continued)

OTHER PUBLICATIONS

Dumas, J.E., Prieto, E.M., Zienkiewicz, K.J., Guda, T., Wenke, J.C., Bible, J., Holt, G., Guelcher, S.A., Balancing the rates of new bone formation and polymer degradation enhances healing of weight-bearing allograft/polyurethane composites in rabbit femoral defects, Tissue Eng, 20: 115-129, 2014. (Year: 2014).*

(Continued)

*Primary Examiner* — Megan Y Wolf
(74) *Attorney, Agent, or Firm* — Norton Rose Fulbright Canada

(57) ABSTRACT

A synthetic bone graft is described which is adapted to be received within a bone defect and which is structurally load-bearing. The bone graft comprises an entirely synthetic graft body corresponding in shape and size to the bone defect. The graft body is composed of a plurality of superimposed multilayered structures, each of the multilayered structures having a biopolymer layer joined to a biomineral layer to define an interface therebetween. The biomineral layer has a stiffness that is greater than that of the biopolymer layer, and the biopolymer layer has a toughness that is less than that of the biomineral layer.

14 Claims, 5 Drawing Sheets

(51) Int. Cl.

| | |
|---|---|
| *B29C 67/24* | (2006.01) |
| *A61L 27/24* | (2006.01) |
| *A61L 27/22* | (2006.01) |
| *B29C 33/38* | (2006.01) |
| *B33Y 80/00* | (2015.01) |
| *B33Y 10/00* | (2015.01) |
| B29L 31/00 | (2006.01) |
| *A61F 2/30* | (2006.01) |

(52) U.S. Cl.
CPC .............. *A61L 27/222* (2013.01); *A61L 27/24* (2013.01); *B29C 33/3835* (2013.01); *B29C 67/24* (2013.01); *B33Y 10/00* (2014.12); *B33Y 80/00* (2014.12); A61F 2002/30014 (2013.01); A61F 2002/30293 (2013.01); A61F 2002/30948 (2013.01); A61F 2002/30957 (2013.01); A61F 2002/30962 (2013.01); A61F 2002/30971 (2013.01); A61F 2210/0076 (2013.01); A61F 2310/00293 (2013.01); A61F 2310/00359 (2013.01); A61L 2430/02 (2013.01); B29K 2089/00 (2013.01); B29K 2995/0082 (2013.01); B29L 2031/7532 (2013.01)

(56) References Cited

U.S. PATENT DOCUMENTS

| | | | | |
|---|---|---|---|---|
| 5,899,939 | A * | 5/1999 | Boyce | A61F 2/28 523/113 |
| 8,012,501 | B2 * | 9/2011 | Kerr | A61F 2/28 424/426 |
| 2004/0062786 | A1 * | 4/2004 | Ascenzi | A61B 17/58 424/423 |
| 2007/0083268 | A1 * | 4/2007 | Teoh | A61F 2/2875 623/17.19 |
| 2014/0044948 | A1 * | 2/2014 | Tanaka | A61L 15/325 428/220 |
| 2015/0352247 | A1 * | 12/2015 | Jie | A61L 27/10 424/426 |

OTHER PUBLICATIONS

Chan RK, Siller-Jackson, Verrett AJ, Wu J, Hale RG., Ten years of war: A characterization of craniomaxillofacial injuries incurred during operations, Enduring Freedom and Iraqi Freedom, Journal of Trauma and Acute Care Surgery 2012; 73:S453-S8.
Pilia M, Guda T, Appleford M., Development of composite scaffolds for load-bearing segmental bone defects, BioMed research international 2013; 2013:458253.
Ritchie RO, Buehler MJ, Hansma P., Plasticity and toughness in bone, Physics Today, 2009; 62:41-7.
Koester KJ, Ager JW, III, Ritchie RO.,The true toughness of human cortical bone measured with realistically short cracks, Nature Materials 2008; 7:672-7.
Peterlik H, Roschger P, Klaushofer K, Fratzl P., From brittle to ductile fracture of bone, Nature Materials 2006; 5:52-S.
Fratzl P, Gupta HS, Fischer FD, Kolednik O., Hindered crack propagation in materials with periodically varying Young's modulus—Lessons from biological materials, Advanced Materials 2007; 19:2657.
Clegg WJ, Kendall K, Alford NM, Button TW, Birchall JD., A Simple Way to Make Tough Ceramics, Nature 1990; 347:455-7.
Chan HM., Layered ceramics: Processing and mechanical behavior, Annual Review of Materials Science 1997; 27:249-82.
Gerhart TN, Miller RL, Kleshinski SJ, Hayes WC., In vitro characterization and biomechanical optimization of a biodegradable particulate composite bone cement, Journal of Biomedical Materials Research 1988; 22: 1071-82.
Cook SD, Barrack RL, Santman M, Patron LP, Salkeld SL, Whitecloud TS., Strut allograft healing to the femur with recombinant human osteogenic protein-1, Clinical Orthopaedics and Related Research 2000: 47-57.

* cited by examiner

MULTILAYERED BONE GRAFT AND METHOD OF MAKING SAME

CROSS-REFERENCE TO RELATED APPLICATIONS

The present application claims priority on U.S. Patent Application No. 62/116,612 filed Feb. 16, 2015, the entire content of which is incorporated herein by reference.

TECHNICAL FIELD

The present disclosure relates generally to bone grafts for use in mammals, and, more particularly, to synthetic bone grafts.

BACKGROUND

Treatment of segmental bone loss remains a major challenge. Traditional techniques (e.g., the use of autografts, allografts, etc.) and newer techniques (e.g., recombinant human bone morphogenetic protein) have well-established performance limitations and patient morbidity, as well as safety concerns.

Suitable bone graft materials should ideally: (i) match the mechanical properties of healthy bone in terms of stiffness, strength and toughness to prevent stress shielding and failure; (ii) be biocompatible/osteoinductive/osteoconductive, and (iii) degrade and resorb over time so healthy bone can take over. No known non-autogenous materials exist that can suitable fulfill these three requirements simultaneously. Titanium, which is widely used for orthopedic bone implants, is generally too stiff and does not resorb over time. Calcium phosphate formulations are alternatively used because they are biocompatible and degradable, but they tend to be too stiff and brittle. Collagen-based synthetics can provide a favourable environment for bone regeneration, but are known to give poor structural support.

In addition to the requirements listed above, segmental bone defects in certain regions of the body present additional challenges because their treatment requires grafts with complex three-dimensional geometries.

Some existing materials which are biocompatible and degradable are approved by the U.S. Food and Drug Administration (FDA) for use as implants. They have often served as ingredients to fabricate hybrid bone substitute materials. While certain materials show encouraging results, the range of their applicability is often limited by their fragility. The structure of these biomaterials is typically poorly controlled, and strengthening and toughening mechanisms have not been systematically exploited and optimized.

Furthermore, the fabrication of suitable bone graft materials for large gaps or large defects has been a longstanding challenge. Historically, known materials have only been effective for non-structural bony defects or extremely small and simple segmental defects.

SUMMARY

There is therefore provided a synthetic bone graft adapted to be received within a bone defect, the bone graft comprising an entirely synthetic graft body corresponding in shape and size to the bone defect and being structurally load-bearing, the graft body being composed of a plurality of superimposed multilayered structures, each of said multilayered structures having a biopolymer layer joined to a biomineral layer to define an interface therebetween, wherein the biomineral layer has a stiffness that is greater than that of the biopolymer layer, and the biopolymer layer has a toughness that is less than that of the biomineral layer.

There is also provided a synthetic bone graft material comprising a plurality of superimposed multilayered structures, each of said multilayered structures having a biopolymer layer joined to a biomineral layer to define an interface therebetween, the biomineral layer being formed of a material selected from the group consisting of calcium sulfates and calcium phosphates, and the biopolymer layer being formed of a material selected from the group consisting of collagen and gelatin, wherein the biomineral layer has a stiffness that is greater than that of the biopolymer layer, and the biopolymer layer has a toughness that is less than that of the biomineral layer.

In a further aspect, there is provided a method of making a multilayered bone graft, comprising: forming a multilayered structure including at least one biopolymer layer joined to at least one biomineral layer, including selecting the biomineral layer to be stiffer and tougher than the biopolymer layer; manipulating the multilayered structure to correspond in shape and size to a bone defect to be treated; and hardening the at least one biomineral layer of the multilayered structure to solidify the multilayered graft shaped and sized like the bone defect.

The method as described above may further include selecting the biomineral layer to be at least five times stiffer than the biopolymer layer.

The method as described above may further include forming the multilayered structures by stacking multiple biopolymer and biomineral layers on top of one another.

The method as described above may further include stacking multiple of the biopolymer layers and the biomineral layers, and subsequently compressing the multilayered structures.

The method as described above may further include hydrating and heating the stacked biopolymer and biomineral layers.

The method as described above may further include applying the multilayered structures to a mold surface having a morphology corresponding to the shape and size of the bone defect to be treated, and forming the bone graft.

BRIEF DESCRIPTION OF THE DRAWINGS

Reference is now made to the accompanying figures in which.

DETAILED DESCRIPTION

Figure 1A:
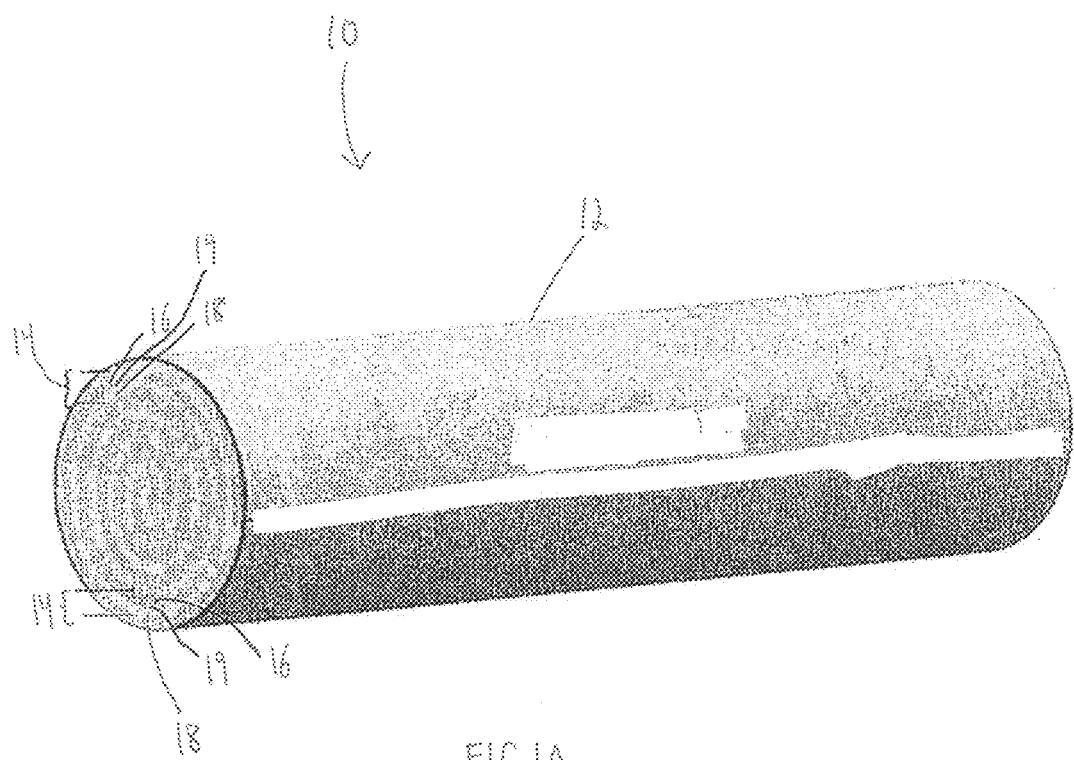
FIG. 1A is a perspective view of a bone graft, according to an embodiment of the present disclosure.

FIG. 1A illustrates a bone graft 10 for the treatment of segmental bone defects, non-structural bone defects, or bone defects which have complex geometries. Although discussed herein in the context of therapies for human bones, the bone graft 10 can also be used to treat bone defects in non-human mammals and/or other animals. The bone graft 10 (or simply "graft 10") can be used to replace or repair damaged bone tissue and help regenerate bone tissue while providing structural strength. The graft 10 as described herein is entirely synthetic, and non-autogenous because it is made from material that is not naturally generated by the patient (i.e. it is not composed of natural bone). The term "synthetic" as used herein is therefore understood to mean a material or combination of materials which do not comprise any natural bone.

More particularly, the synthetic graft 10 is made from non-metallic materials, and is composed of at least two different synthetic materials, such as biominerals and biopolymers, which are arranged in a predetermined layered configuration. As such, the graft 10 is said to be "multilayered", as will be seen in greater detail below. The materials from which the graft 10 is made are biocompatible and biodegradable in the human body, and are selected from materials that have been or may be approved by the relevant governmental authorities (e.g. US Food and Drug Administration, Health Canada, etc.).

The graft 10 is composed of various layers of these materials, which as will be explained below provides a graft that exhibits strength and toughness that are suitable for a bone graft capable of load-bearing properties, so that the graft 10 is able to support mechanical loads once in place within surrounding natural bone. The graft 10 can therefore be used for segmental defects or contoured into patient-specific or generic geometries to treat areas of bone loss that may otherwise be difficult to treat.

The graft 10 includes a graft body 12 which forms the corpus of the graft 10 and provides structure thereto. As will be seen, the graft body 12 is composed of one or more multilayered structures 14, but this multilayered structure may be formed into a number of different graft shapes, such as the cylindrical shape graft body 12 as shown in FIG. 1A. However, although the graft body 12 shown in FIG. 1A is cylindrical in shape, and defines a diameter and length so as to be particularly adapted for use with cortical bone, the graft body 12 can take any other suitable shape or form. For example, the graft body 12 may be cannulated, i.e. it may have a central bore or canal extending at least a partial length, if not the complete length, of the graft body. Indeed, and as is explained in greater detail below, the graft body 12 can be used as a bone substitute for any bone geometry, and thus is able to be shaped and/or formed into any number of different shapes, sizes, etc. The graft body 12 may be a universally applicable component for a bone substitute, or can be custom-designed to a patient-specific geometry. Regardless of its degree of customisation, the graft body 12 is provided with a shape and size which corresponds to that of the bone defect that requires replacement or repair. The present bone graft 10 has been found to be particularly well adapted for filling large bone defects (e.g. greater than about 2.5 cm).

Figure 1B:
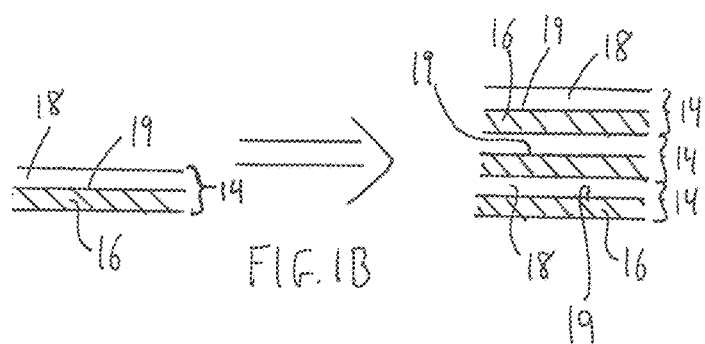
FIG. 1B is a schematic illustration of a single multilayered structured and a plurality of superimposed multilayered structures, which are used in the composition of the bone graft of FIG. 1A.

As noted above, the graft body 12 of the bone graft 10 is made of one or more multilayered structures 14, an example of which is shown in FIG. 1B. Each one of the multilayered structures 14 includes generally at least two superimposed, or sandwiched, layers. More particularly, each of the multilayered structures 14 includes a biomineral layer 16 and a biopolymer layer 18, which are sandwiched together. Each of these multilayered structures 14, composed of the biomineral layer 16 and the biopolymer layer 18, forms a portion of the graft body 12. The number and configuration of the multilayered structures 14 will affect the overall material properties of the graft body 12, and therefore the number of multilayered structures 14 is selected based on the particular requirements of the bone graft 10. Each multilayered structure 14 can have substantially homogeneous material properties, or can be heterogeneous, such that it has different material properties at different locations in the multilayered structure 14 (e.g. a gradient where the properties are different at the middle versus its ends). These differing zones can be formed during the manufacturing process by applying more or less pressure.

The term "biopolymer" as used herein is understood to mean one or more polymers produced by biological organisms and subsequently harvested and purified to make them suitable as biocompatible materials. Such biopolymers also include synthetic polymers which are biocompatible and/or which can degrade in physiological conditions. Examples of suitable biopolymers include, but are not limited to, collagen, gelatin, and mixtures thereof. The biopolymer layer 18 forms a sheet, spread, or thickness of a biopolymer material within each multilayered structure 14. The biopolymer of the biopolymer layer 18 can be any biocompatible, degradable, and regulatory-body approved material for use with implants, and which serves as a bone substitute material. Some non-limitative examples of suitable biopolymers include collagen, gelatin, and mixtures thereof.

The term "biomineral" as used herein is understood to mean one or more minerals which are fully biocompatible and which can degrade in physiological conditions. Examples of such suitable biominerals include, but are not limited to, calcium phosphates and calcium sulfates. The biomineral of each biomineral layer 16 can be any biocompatible, degradable, and regulatory-body approved material for use with implants, and which serves as a bone substitute material. Some non-limitative examples of suitable biominerals include calcium sulfates and calcium phosphates. The biomineral of each biomineral layer 16 does not include metals, alloys thereof, or other materials which do not adequately resorb or degrade when in place. Each of the biomineral layer 16 and the biopolymer layer 18 can have a uniform or non-uniform thickness. The biomineral and biopolymer layers 16, 18 are joined, bonded, or fused together and combined during the manufacturing process such that multilayered structure 14 can be used as a unitary object.

Referring still to FIGS. 1A-1B, the bone graft 10 is accordingly composed of a number of the multilayered structures 14, each of which structures 14 includes at least a biomineral layer 16 and a biopolymer layer 18 sandwiched together. The biopolymer layer 18 is designed to be weaker than the biomineral layer 16 (or in other words, the biomineral layer 16 is stronger than the biopolymer layer 18). In one particular embodiment, the stiffness of the biopolymer layer is five times lower than that of the biomineral layer. The biopolymer can alternately be softer, but not stiffer, than the value provided by this guideline.

The graft body 12 can be formed as an integrally formed, one-piece structure, that is made up of several multilayered structures 14, each accordingly defining having multiple surfaces and thus interfaces 19 therebetween. In one exemplary embodiment, at least one of these interface surfaces measures about 2.5 cm or more in length. In the embodiment of FIG. 1, the cylindrical bone graft 10 may have a total length of 16 mm.

Figure 5:
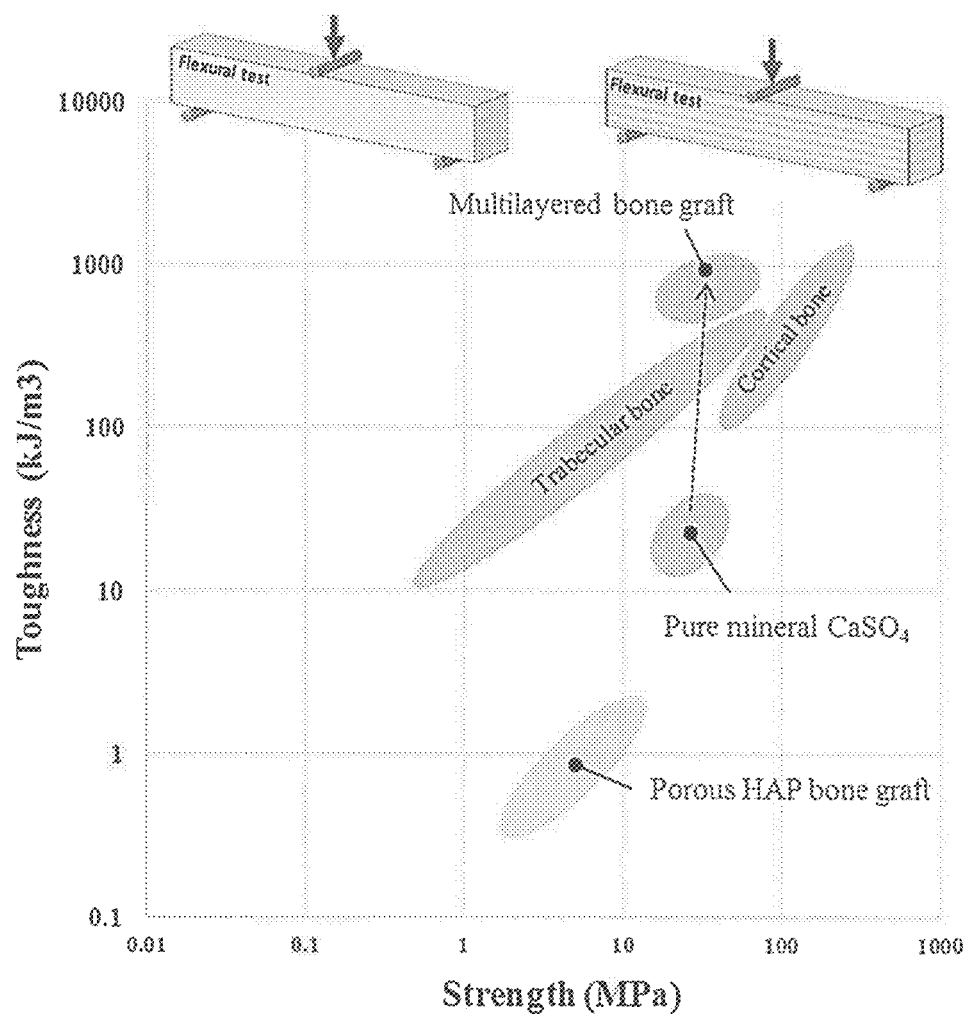
FIG. 5 is a graph depicting toughness vs. strength of the bone graft of FIG. 1A relative to other materials.

Referring now to FIG. 5, the graft 10 having a plurality of the multilayered structures 14 has relatively high strength and toughness properties, such that it is suitable for segmental or structural bone substitution. For example, the total strength of the graft body 12 may be in the 10 to 100 MPa range, and in a particular embodiment the total strength of the graft 10 is between 25 and 30 MPa. With respect to its energy absorption capabilities, the graft body 12 as described herein may have a total impact resistance, or total toughness, in the range of 500 to 1000 kJ/m$^3$. The strength and toughness values in this particular embodiment were obtained during testing carried out on a graft 10 having a total of nine layered materials, namely five hard biomineral layers 16 and four softer biopolymer layers 18, although it is to be understood that more or less layers 16 and 18 may be employed, thereby providing more or less combined multilayered structures 14. The inventors however believe that providing more layers may not necessarily significantly increase the overall strength and toughness values provided above for the exemplary embodiment composed of nine layers. These strength and toughness values allow the graft 10 to be used to fill or treat relatively large bone defects, which has not been the case with known implants.

As seen in FIG. 5, the strength and toughness (i.e. impact resistance) values provided by the present bone graft 10 are significantly higher than for several bone graft materials currently in use, for example porous HAP bone graft and pure mineral CaSO$_4$, and also provide at least improved toughness relative to other more resilient bone replacement materials, such as Trabecular™ bone.

The strength and toughness of the graft 10 may result from its one or more multilayered structures 14. More particularly, the biomineral and biopolymer layers 16, 18 engage one another along an interface 19, which is the surface forming the boundary between the biomineral and biopolymer layers 16, 18. When the graft 10 is exposed to flexural stress or deformation, any cracks which may form in the graft 10 may be deflected either into the softer biopolymer layer 18 and/or along the interfaces 19 between the biomineral and biopolymer layers 16, 18 in each multilayered structure 14. Accordingly, the cracks may propagate into the biopolymer itself (i.e. cohesive crack propagation) or they may propagate at the interface between the biopolymer and the biopolymer (adhesive crack propagation), or they may propagate in a mixed mode, altering between cohesive and adhesive crack propagation modes.

More particularly, it has been observed that the cracks which may form are deflected along the interfaces 19 and/or into the softer biopolymer layer 18, and thus may not propagate through the biomineral layers 16. To ensure crack deflection along the layers of biopolymer 18, and/or along the interfaces between the biopolymer layers 18 and the biomineral layers 16, the toughness of the biopolymer layers 18 should not exceed one-quarter (¼) of the toughness of the biomineral layers 16. Stated differently, the biomineral layer 16 may be at least four times tougher than the biopolymer layer 18. This deflection along the layers of biopolymer 18 increases the distance that cracks must travel before they can cause a failure of the graft 10, which also increases the amount of energy that the graft 10 can absorb before failing. As a result, the bone graft 10 is able to bear loads which are much higher than most known bone graft materials.

The multilayered structures 14 of each graft 10 can therefore absorb more energy (and thus more stress) than most known single-layer constructions, because any cracks deflected along the interfaces 19 between each of the layers 16 and 18 of each multilayered structure 14, and/or between the corresponding interfaces between adjacent multilayered structures 14, require more energy before such cracks pose a problem to the structural integrity of the graft 10.

For example, it has been observed that stacked multilayered structures 14 exhibit strength which is 4.5 times lower than the biomineral alone, but 63 times stronger than the biopolymer alone. It has also been observed that stacked multilayered structures 14 absorb two times more energy than gelatin, and up to 322 times more energy than the biomineral. The multilayered structures 14 therefore contribute to increasing the overall strength of the graft body 12, and thus, of the graft 10 itself.

The phenomenon of crack deflection has been observed in natural bone. Natural bone is several orders of magnitude tougher than the brittle mineral of which it is made. Its material toughness is in part derived from its ability to deflect cracks along weaker interfaces, for example those provided by the cement lines at the periphery of osteon in cortical bone and of bone packets in lamellar bone. Crack deflection increases the crack path, which generates toughness. This configuration also generates toughening by crack bridging, a powerful mechanism where the fractured layers interact and exert a closure force on the crack faces. At smaller scales, the weak interfaces between lamellae also provide weak interfaces, with the ability to deflect incoming cracks and generate toughness. In addition, the interfaces between the lamellae are significantly softer than the lamellae themselves, which generates periodically varying modulus and hinders crack propagation.

Figure 2:
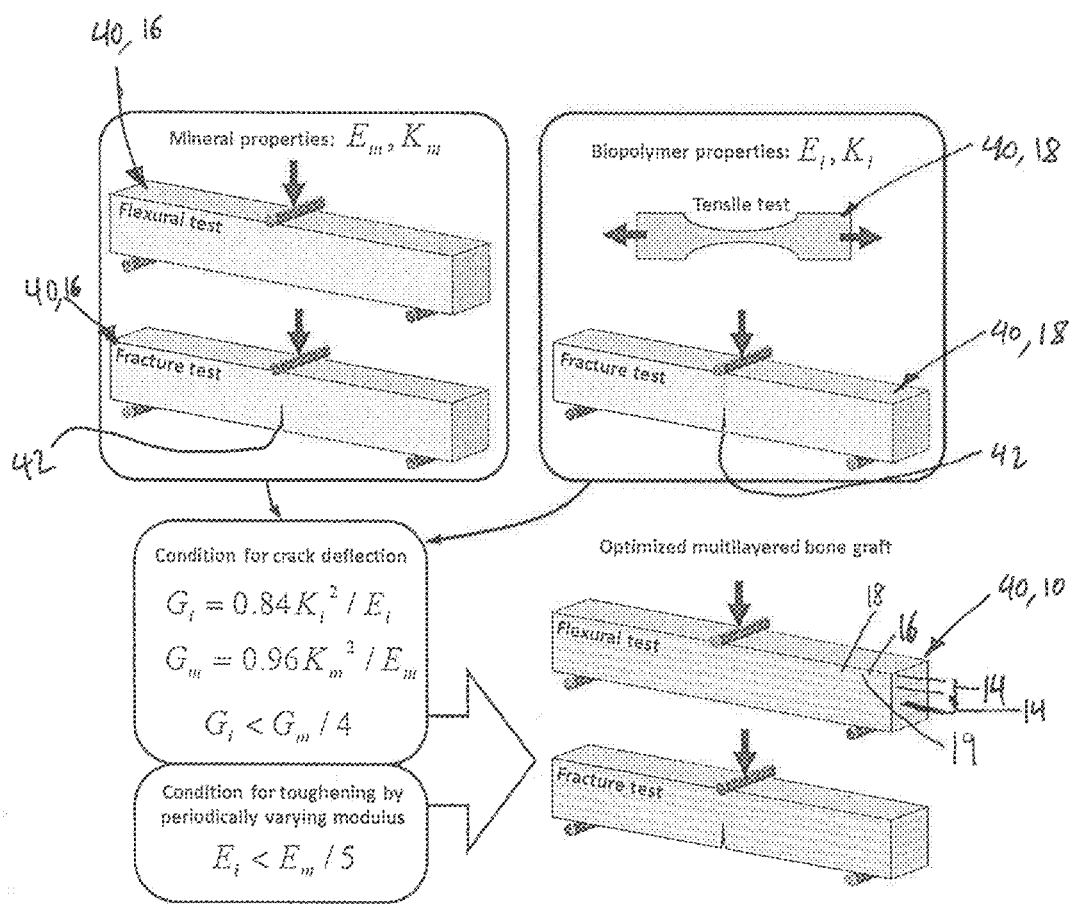
FIG. 2 is a schematic illustration of techniques for testing the strength and toughness of the bone graft of FIG. 1A.

Referring now to FIG. 2, to verify whether the graft 10 disclosed herein can provide adequate strength and toughness, a sample of the graft 10 was subjected to flexural and fracture testing. Flexural deformation is believed to be a suitably representative loading mode for bone grafts. In a flexural test, samples of the graft 10 shaped in the form of a beam 40 were tested in three-point bending to measure the flexural strength of the sample. In a fracture test, pre-cracks 42 were formed in the beam 40 of the sample graft 10 using a laser. The sample was then tested in three-point bending.

FIG. 2 schematically illustrates such flexural and fracture testing of the bone graft 10 formed in as a beam 40 for the purposes of this mechanical testing. It has been observed that the desired crack deflection will occur along the interface 19 if the relationship between the biomineral and biopolymer layers 16, 18 in each multilayered structure 14 is:

$$G_i < G_m/4,$$

where $G_i$ and $G_m$ are the critical strain energy release rates for the biopolymer layer 18 and for the biomineral layer 16, respectively. This relationship may result in a crack intersecting the weaker layer (typically the biopolymer layer 18) at 90° being deflected along the interface 19.

Another technique for assessing crack propagation involves comparing the moduli of elasticity of the biomineral and biopolymer layers 16, 18. It has been observed that materials with a periodically varying modulus of elasticity can significantly increase toughness by decreasing the crack driving force in the softer layers, and that this effect becomes significant when the soft interfaces (i.e. the softer biopolymer layers) are five times softer than the rest of the material, as per the following relationship:

$$E_i < E_m/5,$$

where $E_i$ and $E_m$ are the modulus of elasticity for the biopolymer layer 18 and for the biomineral layer 16, respectively. The modulus of elasticity is a measure of stiffness of the material. Accordingly, based on the above it has been found that by ensuring that the biomineral layer 16 is at least five times stiffer than the biopolymer layer 18, the overall bone graft provides desired levels of load-bearing capabilities. In one particular embodiment, the stiffness ($E_i$) of the biopolymer 18 is in the range of 1 to 10 GPa, and the stiffness ($E_m$) of the biomineral 16 is in the range of 50 to 200 GPa. The exact values of the respective stiffness of each will vary, and may depend on the specific composition of the materials and on the processing techniques employed in their manufacture.

As shown in FIG. 2, the modulus of elasticity relationship may be determined from the critical strain energy relationship, or vise versa, using the following equations:

$$G_i = 0.84\ K_i^2/E_i,\ \text{and}\ G_m = 0.96\ K_m^2/E_m.$$

The inventors have determined that if a bone graft satisfies these relationships, it may have the requisite strength, and toughness and/or stiffness to be used for segmental or structural bone substitution. In the case of the presently described bone graft 10, the graft 10 formed of the above-described multilayered structures 14 was found to satisfy these relationships, and thus provides the desired crack deflection.

In other words, the bone graft 10 of the present disclosure is composed of one or more multilayered structures 14, each formed of a biomineral layer 16 and a biopolymer layer 18, and wherein the biopolymer layers 18 are at least five times softer than the biomineral layers 16 (or, stated differently, wherein the stiffness of the biomineral layer 16 is at least five times greater than the stiffness of the biopolymer layer 18), and/or wherein the toughness (or critical strain energy) of the biopolymer layers 18 is at least four times less than the toughness of the biomineral layers 16 (or, stated differently, wherein the biomineral layer 16 is at least four times tougher than the biopolymer layer 18).

In at least one embodiment, at least four multilayered structures 14 are provided in the body 12 of the bone graft 10, and therefore there exists at least four biomineral layers 16 and at least four biopolymer layers 18. In one particular embodiment, nine total layers 16, 18 are provided in the body 12 of the bone graft, namely 5 harder biomineral layers 16 and four softer biopolymer layers 18. It is therefore to be understood that there may be un-even, or different, total number of biomineral layers 16 and biopolymer layers 18 in the presently described bone graft 10. The strength, stiffness and/or toughness relationships may also be used to optimize the multilayered bone graft 10. In particular, they can help to ensure that the interfaces 19 are weak enough compared to the biomineral to ensure crack deflection, and soft enough to ensure toughening by periodically varying moduli of elasticity.

Various techniques can be used to increase the strength and toughness of the graft 10 and its layers. For example, a biopolymer layer 18 made of gelatin may be stiffened and toughened by increasing its thickness or by the addition of collagen fibrils and/or by crosslinking with paraformaldehyde. Similarly, the toughness of the biomineral can be increased by the addition of gelatin, or by the addition of collagen fibrils which act as short fiber reinforcements for the biomaterial.

There is also disclosed a method for making a multilayered bone graft 10, such as the one described above. The method allows for the formation of a multilayered flexible tape which can be easily manipulated to create bone substitutes for any bone geometry.

The method includes forming a multilayered structure which includes one or more biopolymer layers, and one or more biomineral layers, such as those described above. The formation of this multilayered structure creates the "building block" for the multilayered bone graft. It can be formed by depositing a layer of "green" (i.e. un-sintered) biomineral such as calcium phosphate on a backing tape of a relatively soft biopolymer, which can be a mixture of gelatin and collagen.

Figure 3:
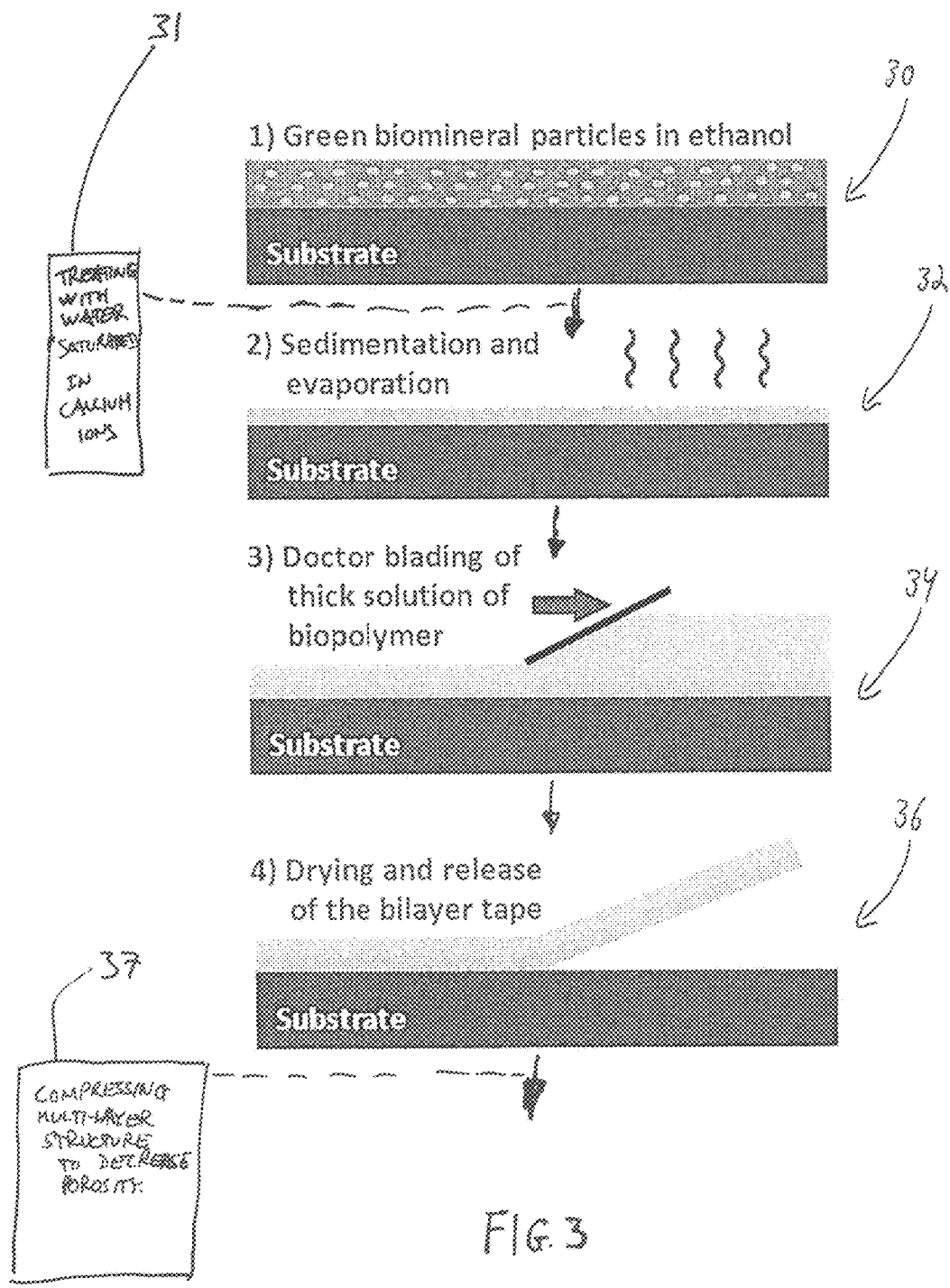
FIG. 3 is a schematic illustration of the formation of a bilayer tape of biomineral and biopolymer, which is used in the composition of the bone graft of FIG. 1A.

Referring to FIG. 3, a slurry of unhardened "green" biomineral particles, such as calcium phosphate particles (DCP or TTCP) and/or calcium sulfate particles, suspended in ethanol are deposited onto a flat substrate made of Teflon® or polycarbonate to facilitate release, shown as 30 in FIG. 3. In one possible embodiment when calcium sulfate is used as the biomineral, an additional step 31 may also be carried out which includes providing water saturated in calcium ions for treating the calcium sulfate particles. This may help to minimize the dissolution of the calcium sulfate and may therefore maximize the strength of the final product.

Upon sedimentation and evaporation, shown at 32 in FIG. 3, a thin layer (i.e. less than about 100 microns) of biomineral will be left on the substrate, thereby forming a biomineral layer 16.

A relatively high concentration solution of the biopolymer can then be applied to the thin biomineral layer 16, shown at 34 in FIG. 3, to form a film of biopolymer 18 over the biomineral layer 16. A doctor-blading technique may then be used to ensure the film of biopolymer 18 has a substantially uniform thickness.

Finally, after a suitable drying or curing period, shown at step 36 in FIG. 3, the multilayered structure 14 can released from the substrate and physically manipulated as required. In the embodiment of FIG. 3, the multilayered structure is a bilayer tape of biomineral and biopolymer.

In one embodiment, an additional step 37 is also carried out, wherein the resulting multilayered structure 14 is compressed in order to decrease the porosity of at least the biomineral layer 16 thereof. This may accordingly enable better control of the thickness and density of the multilayered structure 14 and of the interfaces 19 therein. A hydraulic press may be used, for example, to compress the multilayered structure 14 for the purposes of decreasing the porosity thereof.

The multilayered structure can now be used to form the geometry of the bone substitute. To facilitate such a task, the multilayered structure can be combined with other multilayered structures to achieve a suitable thickness for the bone graft. For example, the bilayer tape of biomineral and biopolymer described above may be assembled into multilayer plates about 2-3 mm thick by stacking between 10 and 50 bilayer tapes atop one another, depending on the tape design. The stacked multiple biopolymer and biomineral layers can then be simultaneously compressed, hydrated, and heated to squeeze out any excess biopolymer and obtain the optimal thickness. The biomineral layers in these plates can be hardened after each bilayer tape is applied, or as a final step by applying a controlled level of moisture.

The method also includes manipulating, manually or by machine, the multilayered structure to correspond in shape and size to a bone defect to be treated. This can be accomplished in many ways depending on the geometry of the bone graft to be formed. For example, cylindrical bone grafts, such as the one shown in FIG. 1A, can be fabricated by rolling a strip of the bilayer tape until the desired diameter is achieved. This diameter can be about 4 mm, for example, and the length of the cylindrical bone graft can be about 16 mm. The roll can then be hardened with moisture or other techniques, and cut into the desired length using a suitable tool. This technique helps to produce a multilayered graft which can resist bending along any direction. Such a cylindrical bone graft can then be implanted to treat large segmental bone defects.

Figure 4:
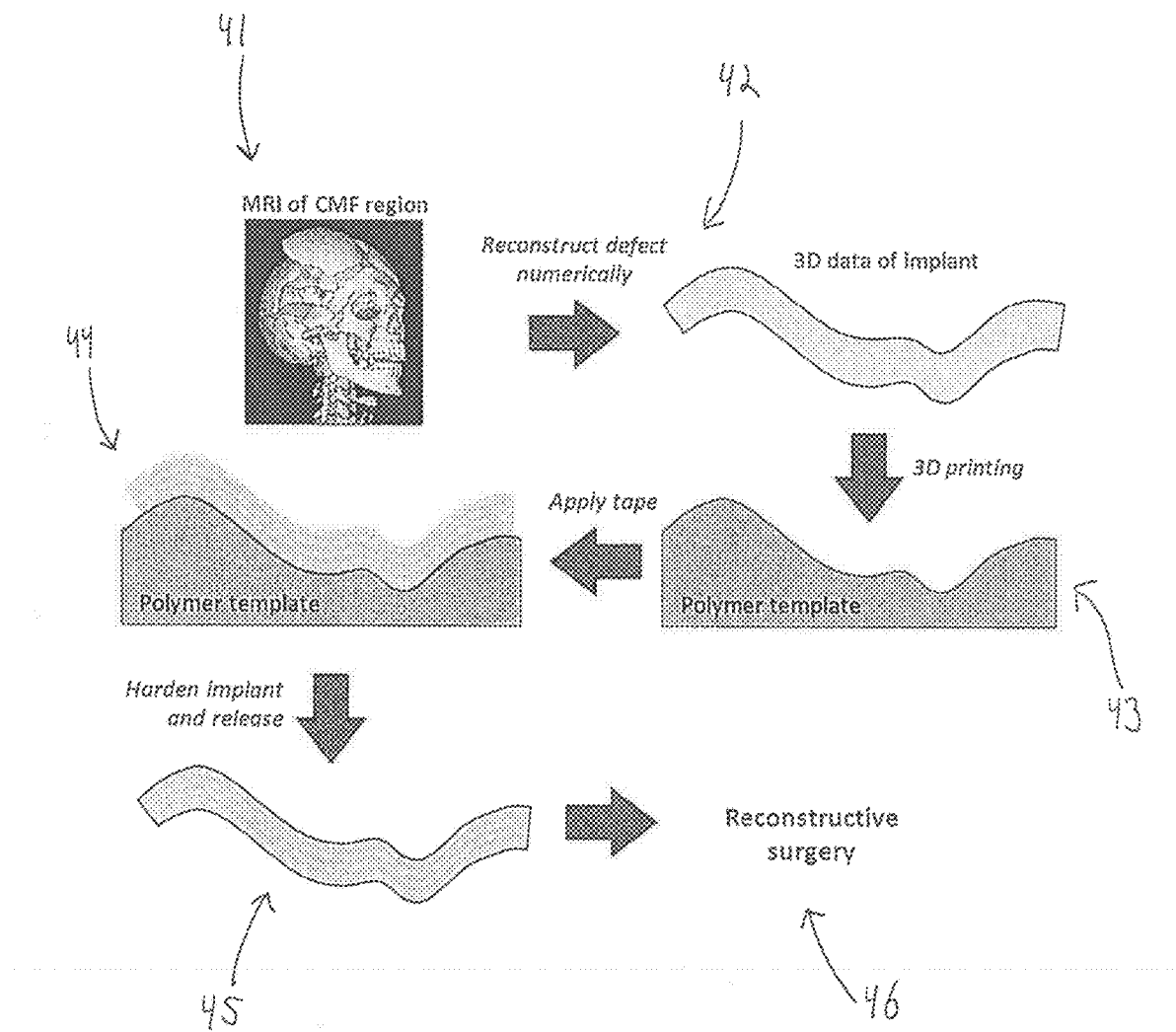
FIG. 4 is a schematic illustration of a multilayered bone graft structure of biomineral and biopolymer in accordance with the present disclosure, used to form a bone graft for use in the craniomaxillofacial (CMF) region.

As mentioned earlier, the multilayered structure can be used to form bone grafts having more complex, three-dimensional geometries. For example, FIG. 4 shows how the multilayered structure can be used to form a bone graft for use in the craniomaxillofacial (CMF) region.

CMF skeletal features have complex three-dimensional geometries. The success of the graft in terms of functionality and esthetics will rely on its ability to exactly duplicate the shape of the missing bone segment. The method disclosed herein provides the ability to match such complex bone geometries. The proposed technique will commence by imaging (e.g. by performing a CT scan or magnetic resonance image (MRI)) of the whole CMF region of the patient, shown as 41 in FIG. 4. By mirroring left-right features, the shape of the missing bone will then be reconstructed numerically, shown as 42 in FIG. 4. The three-dimensional data is then be used to fabricate a polymeric template or mold using a high-resolution additive manufacturing machine, or 3D printer, shown as 43 in FIG. 4. The template/mold conforms exactly to the external side of the missing bone segment. Bilayer tapes are then be applied onto the mold surface and stacked on top of one another until the desired thickness is reached, shown as 44 in FIG. 4. Upon hardening of the biomineral layers, the graft is released from the template, shown as 45 in FIG. 4.

The method also includes hardening the one or more biomineral layers of the multilayered structure to solidify the multilayered graft in its selected shape and size, thereby forming the multilayered bone graft. The graft can then be transferred to the last preparation steps before surgery (sterilization, etc.), shown as 46 in FIG. 4.

It can thus be appreciated that the present disclosure relates to a toughened multilayer bone graft 10 made of biominerals and biopolymers for the treatment of bone defects having any geometry and size. The materials from which the graft 10 is made are fully biocompatible and degradable, and thus satisfy two of the three characteristics for ideal bone grafts. The third characteristic, that of matching the mechanical properties of healthy bone in terms of stiffness, strength and toughness, is also satisfied because of the multilayered structures disclosed herein. Indeed, the multilayered structures disclosed herein provide interfaces between the biomineral and biopolymer layers which are weak enough compared to the biomineral to encourage crack deflection therealong, yet strong enough to ensure toughening by periodically varying modulus.

Furthermore, the method disclosed herein may include innovative fabrication techniques such as layer-by-layer deposition, doctor-blading, 3D printing, or other suitable fabrication techniques. These techniques lead to high microstructural control over the materials used, which in turn lead to improved levels of mechanical performance. In addition, the method allows for an essentially limitless supply of structural bone graft substitute that is designed specifically to allow bone formation while maintaining its toughness. The ability to easily form the multilayered bone graft into any three-dimensional shape using suitable templates/molds makes the method particularly well suited to complex morphologies, such as those found in the CMF region. Furthermore, the method allows for the incorporation of other techniques having high medical potential, such as the incorporation of osteoinductive strontium ions, or pre-constructed vascular systems during the layering process.

Additionally, the bone graft 10 disclosed herein may also comprise therapeutic components or agents therein such as to be used as a means of delivery of such therapeutic components or agents. For example, one or more of antibiotics, bisphosphonates, chemotherapy agents, stem cells, growth factors, etc. can be integrated into the body of the bone graft. This may be done by incorporating such therapeutic components within the body 12 of the bone graft 10, whether this is within a central cannula or other openings formed within the bone graft, or simply as coatings applied to outer surfaces of the bone graft body.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A synthetic bone graft adapted to be received within a bone defect, the bone graft comprising an entirely synthetic graft body corresponding in shape and size to the bone defect and being structurally load-bearing, the graft body being composed of a plurality of superimposed multilayered structures, each of said multilayered structures having a biopolymer layer joined to a biomineral layer to define an interface therebetween, wherein the biomineral layer has a stiffness that is at least five times greater than that of the biopolymer layer, and the biopolymer layer has a toughness that is at least four times less than that of the biomineral layer.

2. The synthetic bone graft of claim 1, wherein the stiffness of the biopolymer layer is between 1 and 10 GPa, and the stiffness of the biomineral layer is between 50 and 200 GPa.

3. The synthetic bone graft of claim 1, wherein the graft body has a strength of between 10 and 100 MPa.

4. The synthetic bone graft of claim 3, wherein the strength of the graft body is between 25 and 30 MPa.

5. The synthetic bone graft of claim 1, wherein a total toughness of the graft body is between 500 and 1000 kJ/m$^3$.

6. The synthetic bone graft of claim 1, wherein the graft body has at least one surface measuring at least about 2.5 cm long.

7. The synthetic bone graft of claim 1, wherein the biopolymer layer is composed of at least one of collagen and gelatin.

8. The synthetic bone graft of claim 1, wherein the biomineral layer is composed of at least one of calcium sulfates and calcium phosphates.

9. The synthetic bone graft of claim 1, wherein the interface between each of said biopolymer layer and said biomineral layer deflects crack propagation therealong and away from the biopolymer layer and the biomineral layer when the bone graft undergoes flexural stress exceeding a flexural stress limit.

10. A synthetic bone graft material comprising a plurality of superimposed multilayered structures, each of said multilayered structures having a biopolymer layer joined to a biomineral layer to define an interface therebetween, the biomineral layer being formed of a material selected from the group consisting of calcium sulfates and calcium phosphates, and the biopolymer layer being formed of a material selected from the group consisting of collagen and gelatin, wherein the biomineral layer has a stiffness that is at least five times greater than that of the biopolymer layer, and the biopolymer layer has a toughness that is at least four times less than that of the biomineral layer.

11. The synthetic bone graft material of claim 10, wherein the stiffness of the biopolymer layer is between 1 and 10 GPa, and the stiffness of the biomineral layer is between 50 and 200 GPa.

12. The synthetic bone graft material of claim 10, wherein said synthetic bone graft material has a strength of between 10 and 100 MPa.

13. The synthetic bone graft material of claim 12, wherein the strength of said synthetic bone graft material is between 25 and 30 MPa.

14. The synthetic bone graft material of claim 10, wherein a combined toughness of said plurality of superimposed multilayered structures is between 500 and 1000 kJ/m$^3$.

* * * * *